United States Patent [19]
Martin

[11] Patent Number: 5,938,665
[45] Date of Patent: Aug. 17, 1999

[54] LOW FRICTION SAW SLOT

[75] Inventor: Troy D. Martin, Pierceton, Ind.

[73] Assignee: Depuy Orthopaedics, Inc., Warsaw, Ind.

[21] Appl. No.: 08/918,790

[22] Filed: Aug. 25, 1997

[51] Int. Cl.⁶ .................................................. A61B 17/56
[52] U.S. Cl. ................................................. 606/88; 606/87
[58] Field of Search ................................ 606/88, 89, 87, 606/86, 80, 82, 79

[56] References Cited

U.S. PATENT DOCUMENTS

| | | |
|---|---|---|
| D. 272,853 | 2/1984 | Buechel et al. . |
| D. 272,854 | 2/1984 | Witte et al. . |
| 4,722,330 | 2/1988 | Russell et al. ............... 606/88 |
| 4,738,253 | 4/1988 | Buechel et al. . |
| 4,738,254 | 4/1988 | Buechel et al. . |
| 5,178,626 | 1/1993 | Pappas . |
| 5,490,854 | 2/1996 | Fisher et al. . |
| 5,507,820 | 4/1996 | Pappas . |
| 5,611,802 | 3/1997 | Samuelson et al. ............... 606/86 |
| 5,643,272 | 7/1997 | Haines et al. ............... 606/80 |
| 5,683,397 | 11/1997 | Vendrely et al. . |
| 5,722,978 | 3/1998 | Jenkins, Jr. ............... 606/87 |

*Primary Examiner*—Guy V. Tucker

[57] ABSTRACT

An instrument is provided in accordance with the present invention for guiding the resection of the bone. Instrument includes a saw guide formed to include a slot. The slot is defined by an upper guide surface and lower guide surface. Guide surfaces are intermittent surfaces to provide a low-friction saw guide surface. Guide surfaces form waves, the upper surfaces of which lie in a common plane.

22 Claims, 3 Drawing Sheets

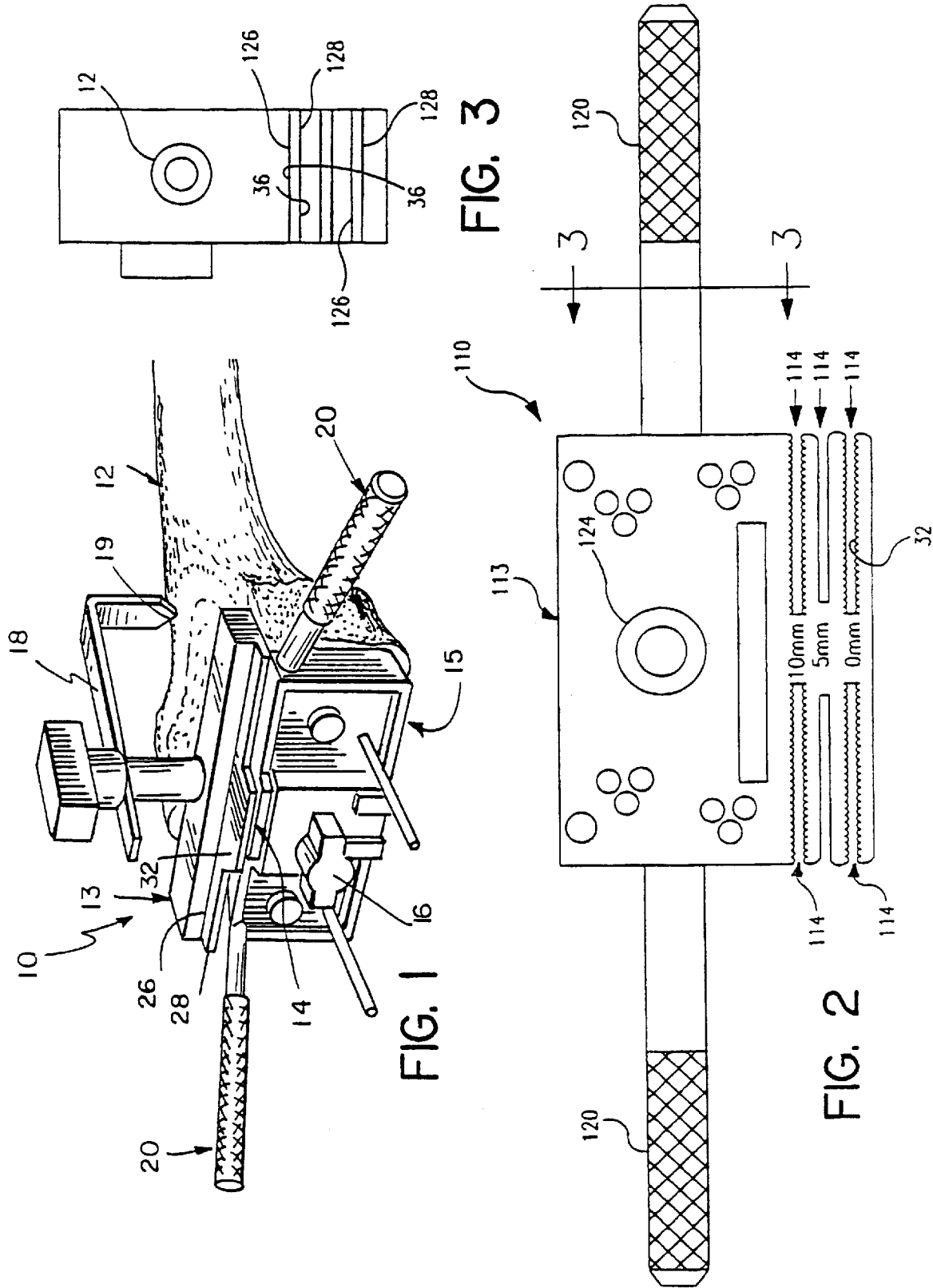

5,938,665

LOW FRICTION SAW SLOT

BACKGROUND OF THE INVENTION

The present invention relates to surgical instruments, and particularly to guides for saw blades used in bone resection.

During various surgical procedures such as implantation of prosthetic knee joints, ankle joints, shoulder joints, finger joints, etc., it is often necessary to make cuts or resections of bone in order for the prosthetic device to be implanted. Typically, these resection procedures involve connecting cutting blocks to the bone using intermedulary rods, screws or the like, and resecting portions of the bone by cutting along a guide path defined by guides that are formed in the cutting blocks. The guide paths formed in the cutting block guide the surgeon's saw blade in a predetermined direction, usually along a straight line, with respect to the mounted cutting block. Once the bone has been properly resected in the appropriate locations, the prosthetic device can then be secured to the bone and the implantation procedure can be completed.

The prior art includes different types of guides for producing a cut or resection in an anatomical structure relative to some reference plane or line. See, for example, U.S. Pat. No. 4,738,253 and U.S. Des. Pat. Nos. 272,853 and 272,854. However, the guides that are currently known have a number of problems. For example, some of the current cutting guides include a single guide surface (made of stainless steel or the like) upon which a saw blade rests as the saw blade is reciprocated or oscillated along the cutting path. As the resection is being made, the saw blade is pressed against the single-sided guide surface and the saw blade has a tendency to bend or bow as the resection is being made. To solve this problem, more recent guides include slots for guiding the saw blade. The saw blade is thus bounded on both sides and can reciprocate within the slot so that the amount of saw blade bowing is minimized.

However, both single-sided guides and slot guides currently in use include a smooth guide surface (or surfaces), usually made of stainless steel, upon which the saw blade travels as it reciprocates or oscillates along the desired cut path. As a result, the saw blade has a tendency to bind or gall against the smooth surface because there is a lot of friction. This in turn causes the bone resections to be less accurate and more difficult because the saw blade is over-stressed. Thus, surgeons who perform bone resections would appreciate a cutting block that included a low-friction guide surface because the bone could be resected more easily and more accurately if the saw blade did not bind, gall, or bow.

SUMMARY OF THE INVENTION

According to the present invention, an instrument for guiding the resection of a bone is provided. The instrument includes a saw guide formed to include a slot for receiving and guiding a saw blade. The slot has an irregular saw blade engaging surface for contacting the saw blade and reducing friction. Preferably, the irregular surface is defined by a plurality of waves, the upper surfaces of which lie in a common plane. However, the irregular surface may also be defined by bumps, spikes, or any other geometric configuration so long as the irregular saw blade engaging surface reduces friction.

In a second embodiment, a saw guide for use with a surgical instrument to resect a bone is provided. The saw guide includes a body and a plurality of waves extending outwardly from the body. The plurality of waves define an irregular saw blade engaging surface for guiding a saw blade and reducing friction. Preferably, in the second embodiment, the body is a block having a slot formed therein with a second and opposing blade engaging surface parallel to and spaced apart from the first engaging surface, the second surface being defined by a plurality of bumps.

In a third embodiment of the present invention, a process for resecting a bone is provided. The process involves drilling a hole in the bone, inserting a guide rod into the hole, attaching a cutting block to the bone using the rod, and manipulating a saw blade along the cutting block to resect the bone. The cutting block includes an irregular guide surface so that as the saw blade is manipulated along the irregular guide surface, friction is reduced.

Additional features and advantages of the invention will become apparent to those skilled in the art upon consideration of the following detailed description of preferred embodiments exemplifying the best modes of carrying out the invention as presently perceived.

BRIEF DESCRIPTION OF THE DRAWINGS

The detailed description particularly refers to the following figures in which:

FIG. 1 is a perspective view of an instrument in accordance with the present invention for resecting a bone showing the instrument as it would appear after being mounted to the bone;

FIG. 2 is a front view of an alternative embodiment of an instrument in accordance with the present invention, showing a cutting block including a plurality of saw guides, each having an irregular guide surfaces to reduce friction;

FIG. 3 is a view taken along lines 3—3 of FIG. 2 showing the saw guides extending into the cutting block;

DETAILED DESCRIPTION OF THE DRAWINGS

Figure 4:
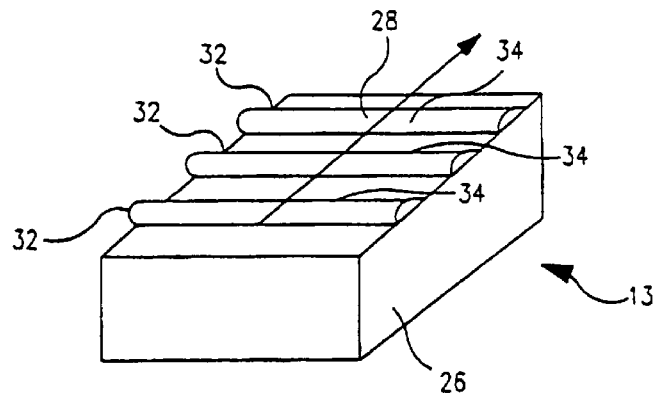
FIG. 4 is a enlarged perspective view of the guide surface of the cutting block of FIG. 2 showing the guide surface being defined by waves.

An instrument 10 for resecting a bone 12 in accordance with the present invention is shown in FIG. 1. Instrument 10 includes a saw guide or cutting block 13 formed to include a slot 14 for receiving and guiding a saw blade (not shown) along a path to resect or cut bone 12. Instrument 10 further includes a mounting block 15 having a pair of handles 20 for maneuvering instrument 10 and a guide rod 16 for connecting mounting block 15 to bone 12. Once a hole (not shown) is drilled into bone 12 and mounting block 15 is connected to bone 12 using guide rod 16, cutting block 13 can be connected to mounting block 15. Then, a resection can be made by reciprocating or oscillating a saw blade (not shown) within slot 14 along the path defined by slot 14.

Instrument 10 also preferably includes a stylus 18 for aligning the depth of the bone cut. Stylus 18 is appended to mounting block 15 and includes a tip 19 that is positioned to touch the lowest part of bone 12 so that a proper resection can be made. With instrument 10 connected to bone 12 and tip 19 of stylus 18 positioned against the lowest part of bone 12, a saw blade (not shown) can be inserted into slot 14 and reciprocated or oscillated along the path defined by slot 14 until bone 12 is completely resected.

Figure 9:
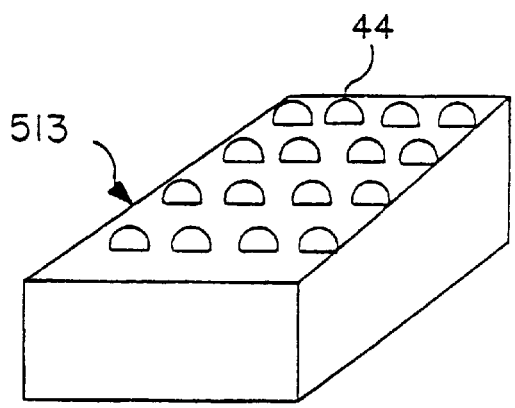
FIG. 9 is a view similar to FIG. 4 of an alternative embodiment of the present invention showing a cutting block having an irregular guide surface being defined by bumps formed on the cutting block.
Figure 8:
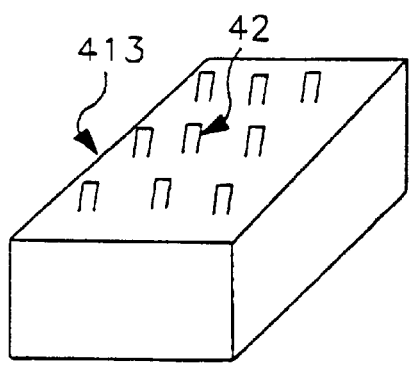
FIG. 8 is a view similar to FIG. 4 of an alternative embodiment of the present invention showing a cutting block having an irregular guide surface being defined by spikes formed in the cutting block.

As shown in FIGS. 1 and 4, cutting block 13 is formed to include waves 32. Further, waves 32 are defined by valleys between the peaks 34. As shown in FIG. 1, slot 14 is defined by an upper guide surface 26 and lower guide surface 28. Guide surfaces 26, 28 are irregular (or intermittent) surfaces in order to provide a low-friction saw guide surface. Upper and lower saw blade guiding surfaces 26,28 define a path in the slot 14 in which a saw blade can be guided. With the saw blade positioned in slot 14, saw blade guiding surfaces 26, 28 guide the saw blade as the saw blade reciprocates or oscillates along the path so that a proper resection can be made. While guide surfaces 26, 28 are illustrated and described it is understood that only one guide surface is suitable for use in the present invention as shown in FIGS. 4, 8, and 9.

Waves 32 may be formed in cutting block 13 using wire cutting techniques that are known in the art. Using the wire cutting techniques, waves 32 are formed into cutting block 13 such that waves 32 are rounded as shown in FIG. 4. In the preferred embodiment, waves 32 are semi-circular and have peaks 34 that define the irregular saw blade engaging surfaces 26, 28. As shown in FIGS. 8 and 9, cutting blocks 413, 513 may also be formed to include spikes 42 or bumps 44 that define the irregular saw blade guiding surfaces 26, 28. Whether the saw blade guiding surface 26 or surfaces 26, 28 are defined by waves 32, spikes 42, or bumps 44, the resultant irregular surfaces 26, 28 reduce friction, galling, and bowing of a the saw blade when a bone resection is performed. It is believed that the surface area of the saw blade guiding surface which engages the saw blade is reduced. Thus, it is within the scope of this invention that a variety of other irregularly shaped surfaces or methods could be used to reduce the saw blade engaging surface area thereby reducing the friction, galling, or bowing of the saw blade during bone resection procedures.

An instrument 110 is an alternative embodiment of the present invention and is shown in FIG. 2. Instrument 110 includes a unitary mounting/cutting block 113. Mounting/cutting block 113 has handles 120 for maneuvering the mounting/cutting block 113 relative to bone 12. Mounting/cutting block 113 is also formed to include a hole 124 for receiving a guide rod 16 to mount the mounting/cutting block 113 to bone 12. Mounting/cutting block 113 is further formed to include a plurality of slots 114. Slots 114 are sized to accommodate a variety of saw blade sizes and shapes.

As shown in FIG. 2, each of the saw guide slots 114 are defined by a pair of upper and lower saw blade engaging surfaces 126, 128. The saw blade engaging surfaces 126, 128 are generally parallel to one another. It is understood, however, that only a single saw blade engaging surface 126 could be used or if multiple saw blade engaging surfaces are used, the surfaces could be configured in a non-parallel relationship that is not substantially straight. Thus, surgeons could create any one of a wide variety of bone resections.

Figure 5:
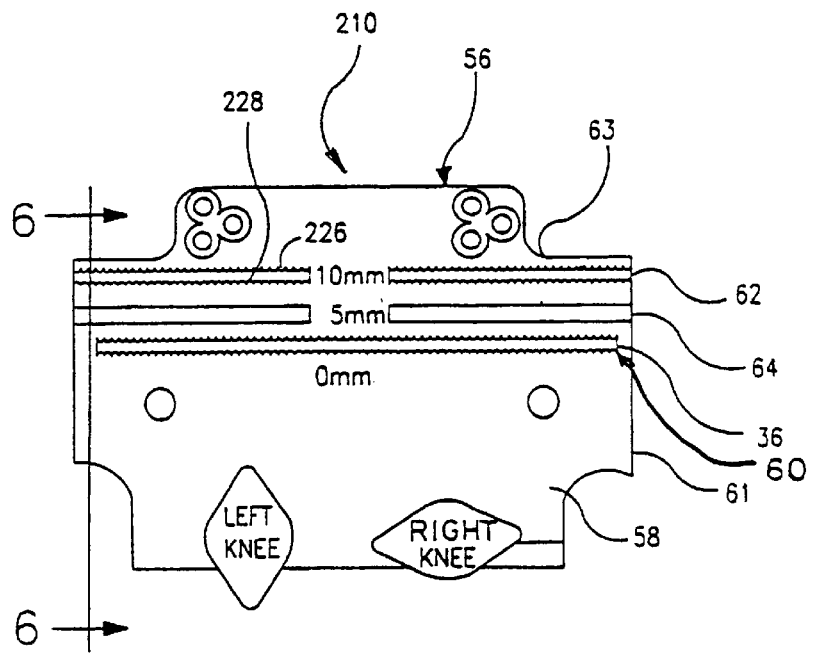
FIG. 5 is a front view of an alternative embodiment of cutting block of FIG. 4 having a plurality of saw guides with irregular guide surfaces.
Figure 6:
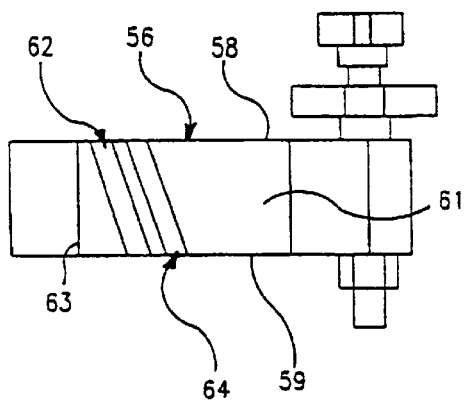
FIG. 6 is a section view of the cutting block taken along lines 6—6 of FIG. 5, showing the saw guides having an angled orientation.

An instrument 210 of an alternative embodiment of the present invention includes a cutting block 56, as shown in FIGS. 5 and 6. Cutting block 56 is similar to the cutting block 13 and mounting/cutting block 113 except that cutting block 56 includes a closed-loop saw guide slot 60 and a pair of open-ended saw guide slots 62, 64. Guide slots 62, 64 are defined by saw guide surfaces 226, 228. Cutting block 56 includes a first face 58, an opposite second face 59, and a side wall 61 extending therebetween. Cutting block 56 further including a top platform 63. Open-ended saw guide slots 62, 64 extend between first and second faces 62, 64 at an angle of about 11° with respect to the top platform 63. Both the open-ended saw guide slots 62 and 64 and the closed-loop saw guide slot 60 can be formed to include waves 32 (FIG. 4), spikes 42 (FIG. 8), and/or bumps 44 (FIG. 9) and may be formed at any angle relative to the cutting block.

Figure 7:
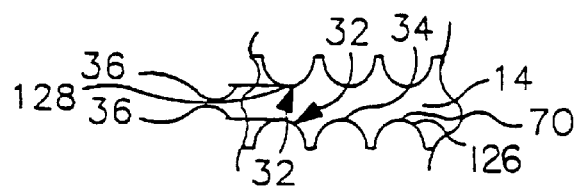
FIG. 7 is an enlarged view of saw guides in the cutting block of FIG. 2, showing the irregular guide surface of the saw guides having waves with flattened top portions.

Waves 32 of FIG. 2 are shown in greater detail in FIG. 7. Peaks 34 of waves 32 include a flattened top portion 70 so that the wear on a saw blade engaging surface 36 will be reduced. Preferably, the flattened top portion 70 is approximately 0.006 inches. Spikes 42 or bumps 44 could also be formed to include flattened top portions to reduce wear.

Although cutting block 13 and cutting block 56 are used in connection with resections performed on ends of femurs in knee replacement surgery, the irregularly-shaped saw blade engaging surfaces 36 formed in cutting blocks 13, 113, 56, 413 and 513 may be used for any bone resection.

Although the present invention has been described in detail with reference to certain preferred embodiments, variations and modifications exist within the spirit and scope of the invention as described and defined in the following claims.

I claim:

1. An instrument for guiding resection of a bone comprising:
    a saw guide providing a slot for receiving and guiding a saw blade;
    said slot having an irregular saw blade engaging surface created by at least two spaced apart valleys in the blade engaging surface for contacting the saw blade and reducing friction.

2. The instrument of claim 1, wherein the irregular surface is defined by a plurality of waves, the upper surfaces of which lie in a common guide plane.

3. The instrument of claim 1, wherein the irregular surface is defined by a plurality of bumps, the upper surfaces of which are flattened to provide a plurality of individual guide surfaces lying in a common plane.

4. The instrument of claim 1, wherein the irregular surface includes peaks and valleys such that the peaks of the bumps define the saw blade engaging surface.

5. The instrument of claim 1, wherein the irregular surface is defined by a plurality of spikes.

6. The instrument of claim 5, wherein the spikes include flattened top portions that define the saw blade engaging surface.

7. For use with a saw blade to resect a bone, an instrument for attachment of the bone and a saw block connected to the instrument for establishing the location and direction of the resection, said block having an intermittent surface created by at lease two spaced apart valleys in the surface for engaging and guiding the blade and reducing friction.

8. The instrument of claim 7, wherein the intermittent surface is defined by a plurality of waves.

9. The instrument of claim 7, wherein the intermittent surface includes peaks and valleys such that the peaks of the bumps define the saw blade engaging surface.

10. The instrument of claim 9, wherein the waves have a flattened top surface to guide the saw blade along the saw blade engaging surface.

11. The instrument of claim 7, wherein the intermittent surface is defined by a plurality of spikes, having flattened top portions that define the saw blade engaging surface.

12. The instrument of claim 7, wherein the intermittent surface is defined by a plurality of bumps.

13. The instrument of claim 7, wherein the intermittent surface defines plane that is substantially flat.

14. A saw guide for use with a surgical instrument to resect a bone, the saw guide comprising:

a body and a plurality of spaced apart valleys extending inwardly into the body and defining an irregular saw blade engaging surface for guiding a saw blade and reducing friction between the saw blade and the engaging surface.

15. The saw guide of claim 14, wherein the body is a block having a slot formed therein with a second and opposing blade engaging surface parallel to and spaced apart from the first said engaging surface, said second surface defined by a plurality of bumps.

16. The saw guide of claim 15, wherein the bumps include peaks and valleys such that the peaks of the bumps define the saw blade engaging surface.

17. The saw guide of claim 15, wherein the bumps have a flattened top surface to guide the saw blade along the saw blade engaging surface.

18. A process for resecting a bone comprising:

drilling a hole in the bone, inserting a guide rod into the hole, attaching a cutting block to the bone using the rod, the cutting block having an irregular guide surface created by at least spaced apart valleys in the guide surface, and manipulating a saw blade along the irregular guide surface to resect the bone along a plane defined by the irregular guide surface.

19. The process of claim 18, wherein the irregular guide surface is a plurality of bumps.

20. The process of claim 19, wherein the bumps have a flattened top surface to guide the saw blade along the saw blade engaging surface.

21. The process of claim 18, wherein the irregular guide surface is a plurality of spikes.

22. The process of claim 21, wherein the spikes have a flattened top surface to guide the saw blade along the saw blade engaging surface.

* * * * *